US009591985B2

(12) United States Patent
Koike et al.

(10) Patent No.: US 9,591,985 B2
(45) Date of Patent: Mar. 14, 2017

(54) BIOLOGICAL INFORMATION DISPLAYING APPARATUS AND BIOLOGICAL INFORMATION DISPLAYING METHOD

(71) Applicant: NIHON KOHDEN CORPORATION, Tokyo (JP)

(72) Inventors: Teruhiro Koike, Tokyo (JP); Yoshinobu Ono, Tokyo (JP); Masahiro Yade, Tokyo (JP); Satoshi Saitoh, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 234 days.

(21) Appl. No.: 14/287,324

(22) Filed: May 27, 2014

(65) Prior Publication Data

US 2014/0378856 A1    Dec. 25, 2014

(30) Foreign Application Priority Data

Jun. 25, 2013  (JP) .................................. 2013-132896

(51) Int. Cl.
*A61B 5/04* (2006.01)
*A61B 5/0452* (2006.01)
*A61B 5/00* (2006.01)

(52) U.S. Cl.
CPC .......... *A61B 5/0452* (2013.01); *A61B 5/7235* (2013.01)

(58) Field of Classification Search
CPC ...................................... A61B 5/7475–5/7485

(Continued)

(56) References Cited

U.S. PATENT DOCUMENTS 6,934,578 B2 *  8/2005  Ramseth ............. G06F 19/3412
                                                                    600/523
7,421,292 B1 *  9/2008  Kroll .................... A61N 1/3621
                                                                    128/903

(Continued)

FOREIGN PATENT DOCUMENTS

JP          9-51880 A        2/1997
WO      2012/158720 A1      11/2012
WO      2013/048980 A1       4/2013

OTHER PUBLICATIONS

The extended European Search Report for the related European Patent Application No. 14172137.3 dated Sep. 4, 2014.

*Primary Examiner* — Amanda Patton
*Assistant Examiner* — Philip C Edwards
(74) *Attorney, Agent, or Firm* — Pearne & Gordon LLP

(57) ABSTRACT

A biological information displaying apparatus includes an analyzing unit and a display unit. The analyzing unit analyzes measured continuous biological information waveforms to detect abnormal biological information waveforms. The display unit simultaneously displays a first waveform group consisting of continuous biological information waveforms including an abnormal biological information waveform which is produced initially in abnormal biological information waveforms that are produced in a duration when the abnormal biological information waveforms detected by the analyzing unit are continued and a biological information waveform which is produced just before the production of the initial abnormal biological information waveform, and a second waveform group consisting of continuous biological information waveforms including an abnormal biological information waveform which is last produced and a biological information waveform which is produced just after the production of the last abnormal biological information waveform.

16 Claims, 4 Drawing Sheets

(58) Field of Classification Search
USPC .......................................................... 600/523
See application file for complete search history.

(56) References Cited

U.S. PATENT DOCUMENTS

| | | | |
|---|---|---|---|
| 2003/0097077 A1* | 5/2003 | Morganroth | A61B 5/0452 600/509 |
| 2004/0102814 A1* | 5/2004 | Sorensen | A61N 1/37247 607/17 |
| 2007/0260147 A1 | 11/2007 | Giftakis et al. | |
| 2008/0125824 A1 | 5/2008 | Sauer et al. | |
| 2011/0077541 A1 | 3/2011 | Dong et al. | |

* cited by examiner

BIOLOGICAL INFORMATION DISPLAYING APPARATUS AND BIOLOGICAL INFORMATION DISPLAYING METHOD

CROSS REFERENCE TO RELATED APPLICATION

This application is based on Japanese Patent Applications No. 2013-132896 filed on Jun. 25, 2013, the contents of which are incorporated herein by reference.

BACKGROUND

The presently disclosed subject matter relates to a biological information displaying apparatus and a biological information displaying method.

A doctor or the like checks a temporal transition of measurement values of biological information waveforms which are produced repeatedly and continuously from the living body of a patient, thereby knowing the condition of the patient to detect an abnormality.

As a technique for easily displaying a desired one of arrhythmia waveforms which are measured biological information waveforms, the following technique is known. In a patient monitoring device, the screen is divided into two areas, a list of a plurality of registered compressed waveforms of arrhythmia is displayed in one of the areas, and one of the listed compressed waveforms which one is designated by the user is enlargedly displayed in the other area. According to the configuration, the user can easily select and designate a desired waveform from the listed compressed waveforms, and therefore a desired one of the measured arrhythmia waveforms can be easily displayed (JP-A-9-051880).

In the case where arrhythmia continuously occurs for a long time, however, a situation often occurs where waveforms before and at the initial timing of the occurrence of arrhythmia, and those just before and after termination of arrhythmia must be compared to each other to check a change of the rhythm. In the above-described prior art, when arrhythmia continuously occurs for a long time, a page turning operation must be performed a number of times in order that waveforms in the vicinity of the initial timing of the occurrence of arrhythmia, and that in the vicinity of the termination of arrhythmia are checked in the waveforms which are enlargedly displayed. This produces a problem in that it is impossible to quickly check a rhythm change in waveforms before and after the occurrence of arrhythmia, and that before and after the termination.

The presently disclosed subject matter has been conducted in order to solve the problem. It is an object of the presently disclosed subject matter to enable a change of the rhythm to be checked easily and instantaneously in the following manner. Namely, abnormal biological information waveforms are detected from continuous biological information waveforms. A first waveform group and a second waveform group are simultaneously displayed. The first waveform group consists of continuous biological information waveforms including: an abnormal biological information waveform which is produced initially in abnormal biological information waveforms that are produced in a duration when abnormal biological information waveforms are continued; and a biological information waveform which is produced just before the production of the initial abnormal biological information waveform. The second waveform group consists of continuous biological information waveforms including: an abnormal biological information waveform which is last produced; and a biological information waveform which is produced just after the production of the last abnormal biological information waveform.

According to the configuration, even in the case where arrhythmia continuously occurs for a long time, the waveforms at the initial timing of and before the occurrence of arrhythmia, and those just before and after termination of arrhythmia can be compared to each other at one time, thereby enabling a change of the rhythm to be checked easily and instantaneously.

SUMMARY

According to the presently disclosed subject matter, the problem can be solved by the following means.

(1) A biological information displaying apparatus having: a analyzing unit which analyzes measured continuous biological information waveforms to detect abnormal biological information waveforms; and a display unit which simultaneously displays: a first waveform group consisting of continuous biological information waveforms including: an abnormal biological information waveform which is produced initially in abnormal biological information waveforms that are produced in a duration when the abnormal biological information waveforms detected by the analyzing unit are continued; and a biological information waveform which is produced just before the production of the initial abnormal biological information waveform; and a second waveform group consisting of continuous biological information waveforms including: an abnormal biological information waveform which is last produced; and a biological information waveform which is produced just after the production of the last abnormal biological information waveform.

(2) A biological information displaying method having: a step (a) of analyzing measured continuous biological information waveforms to detect abnormal biological information waveforms; and a step (b) of simultaneously displaying: a first waveform group consisting of continuous biological information waveforms including: an abnormal biological information waveform which is produced initially in abnormal biological information waveforms that are produced in a duration when the abnormal biological information waveforms detected in the step (a) are continued; and a biological information waveform which is produced just before the production of the initial abnormal biological information waveform; and a second waveform group consisting of continuous biological information waveforms including: an abnormal biological information waveform which is last produced; and a biological information waveform which is produced just after the production of the last abnormal biological information waveform.

Abnormal biological information waveforms are detected from continuous biological information waveforms. Then, a first waveform group consisting of continuous biological information waveforms including: an abnormal biological information waveform which is produced initially in abnormal biological information waveforms which are produced in a duration when abnormal biological information waveforms are continued; and a biological information waveform which is produced just before the production of the initial abnormal biological information waveform, and a second waveform group consists of continuous biological information waveforms including: an abnormal biological information waveform which is last produced; and a biological information waveform is produced just after the production of the last abnormal biological information waveform are simultaneously displayed. According to the configuration, even in the case where arrhythmia continuously occurs for a long time, the waveforms at the initial timing of and before the occurrence of arrhythmia, and those just before and after termination of arrhythmia can be compared to each other at one time. Therefore, a change of the rhythm can be checked easily and instantaneously.

DETAILED DESCRIPTION OF EMBODIMENTS

Hereinafter, a biological information displaying apparatus and method of embodiments of the presently disclosed subject matter will be described in detail with reference to the drawings.

First Embodiment

Figure 1:
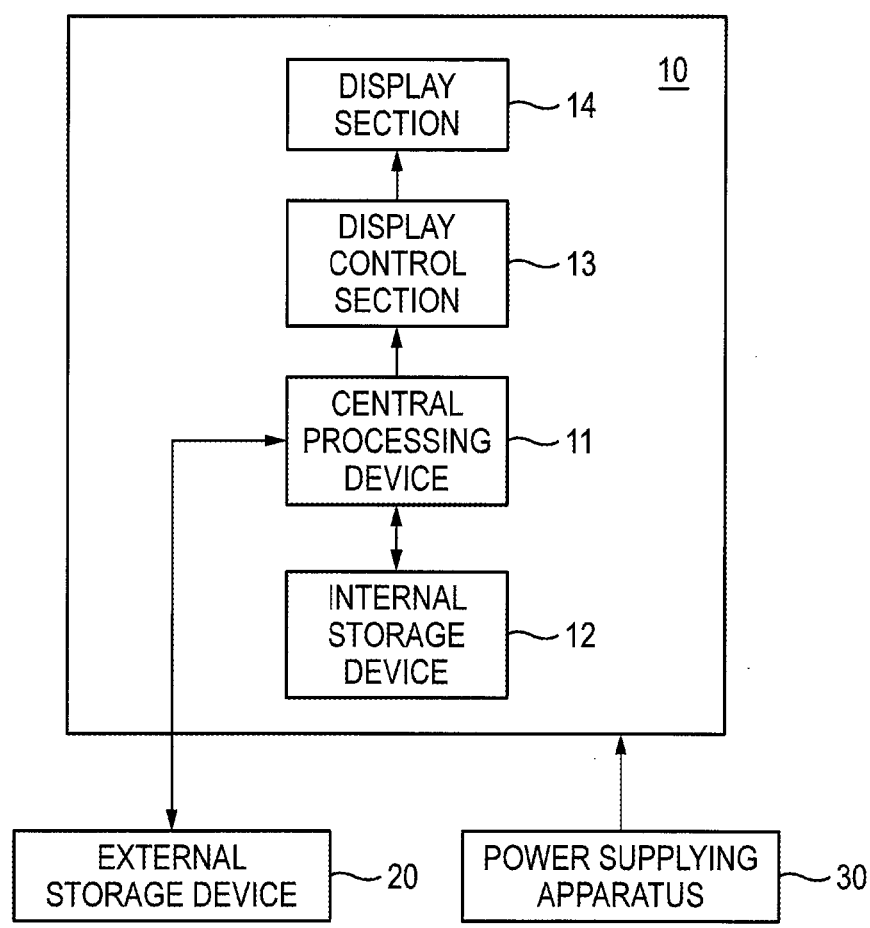
FIG. 1 is a block diagram of a biological information displaying system including a biological information displaying apparatus of a first embodiment of the presently disclosed subject matter.

FIG. 1 is a block diagram of a biological information displaying system including a biological information displaying apparatus of a first embodiment of the presently disclosed subject matter.

As shown in FIG. 1, the biological information displaying system is configured by connecting an external storage device 20 and a power supplying apparatus 30 to the biological information displaying apparatus 10.

The biological information displaying apparatus 10 may be configured by, for example, a personal computer. The external storage device 20 may be configured by an SD memory card in which, when attached to a Holter electrocardiogram monitor or the like, an electrocardiogram that is biological information is recorded, and which is attachable to and detachable from the personal computer. The power supplying apparatus 30 is an apparatus which supplies electric power for driving the biological information displaying apparatus 10, to the apparatus 10, and may be configured so as to have a secondary battery or the like.

When the external storage device 20 is attached to the biological information displaying apparatus 10, the apparatus reads measured biological information which is stored in the external storage device 20, and analyzes the biological information to detect abnormal biological information waveforms is continuous biological information waveforms. The biological information displaying apparatus 10 simultaneously displays: a biological information waveform which is produced initially in abnormal biological information waveforms in a duration when abnormal biological information waveforms are continued; a biological information waveform which is produced just before the production of the initial abnormal biological information waveform; an abnormal biological information waveform which is last produced; and a biological information waveform which is produced just after the production of the last abnormal biological information waveform.

Biological information is a set of biological information waveforms which are physiological information that is periodically produced by a living body, and, for example, an electrocardiogram. However, the biological information is not limited to this, and, for example, may be respiratory waveforms which are used in diagnosis of sleep apnea syndrome and the like. A biological information waveform is a unit waveform constituting biological information, and, for example, an electrocardiogram waveform per heart beat. For example, an electrocardiogram waveform may be defined as a waveform extending from an arbitrary R wave in an electrocardiogram to the next appearing R wave. An abnormal biological information waveform is, for example, an electrocardiogram waveform of arrhythmia (hereinafter, referred to as "arrhythmia waveform").

In the following description, for the sake of simplicity, an electrocardiogram, an electrocardiogram waveform, and an arrhythmia waveform will be used as examples of biological information, a biological information waveform, and an abnormal biological information waveform, respectively.

The biological information displaying apparatus 10 has a central processing device 11, an internal storage device 12, a display control section 13, and a display section 14.

The central processing device 11 constitutes the analyzing unit in the presently disclosed subject matter, and the display control section 13, the display section 14, and the central processing device 11 constitute the displaying unit.

The central processing device 11 may be configured by a CPU (Central Processing Unit).

The central processing device 11 reads a measured electrocardiogram from the external storage device 20 connected to the biological information displaying apparatus 10, and analyzes the electrocardiogram to detect an arrhythmia waveform from continuous biological information waveforms. The central processing device 11 causes a basic waveform pattern of an arrhythmia waveform to be previously recorded in the internal storage device 12, and compares the basic waveform pattern of an arrhythmia waveform with the measured electrocardiogram waveform. An electrocardiogram waveform which is similar to the basic waveform pattern of the arrhythmia waveform is detected as an arrhythmia waveform.

The central processing device 11 detects also that the arrhythmia waveform is continuous. Namely, the central processing device 11 detects an abnormal waveform group consisting of arrhythmia waveforms included in a duration when arrhythmia waveforms are continued. Then, the arrhythmia waveform which is produced initially in the abnormal arrhythmia waveforms included in the abnormal waveform group (hereinafter, the waveform is referred to as "initial arrhythmia waveform"), and that which is produced last (hereinafter, the waveform is referred to as "last arrhythmia waveform") are simultaneously displayed on the display section 14. Namely, the central processing device 11 causes the initial arrhythmia waveform which is produced initially in the abnormal arrhythmia waveforms that are produced in a duration when arrhythmia is continued, and the last arrhythmia waveform which is produced last, to be simultaneously displayed on the display section 14. At this time, the central processing device 11 can cause the initial arrhythmia waveform to be displayed together with an electrocardiogram waveform which is adjacent to the initial arrhythmia waveform, on the display section 14, and the last arrhythmia waveform to be displayed together with an electrocardiogram waveform which is adjacent to the last arrhythmia waveform, on the display section 14. A waveform group consisting of continuous electrocardiogram waveforms including the initial arrhythmia waveform and the electrocardiogram waveform which is adjacent to the initial arrhythmia waveform constitutes a first waveform group. A waveform group consisting of continuous electrocardiogram waveforms including the last arrhythmia waveform and the electrocardiogram waveform which is adjacent to the last arrhythmia waveform constitutes a second waveform group. The first waveform group includes the initial arrhythmia waveform and the electrocardiogram waveform produced just before the production of the initial arrhythmia waveform. The second waveform group includes the arrhythmia waveform which is produced last, and the electrocardiogram waveform produced just after the production of the last arrhythmia waveform.

The number of the electrocardiogram waveform(s) to be displayed together with the initial arrhythmia waveform, and that of the electrocardiogram waveform(s) to be displayed together with the last arrhythmia waveform can be adequately changed in accordance with, for example, a disease suspected in the subject.

In the case where continuous arrhythmia waveforms are intermittently produced, the central processing device 11 causes the initial and last arrhythmia waveforms included in each abnormal waveform group, to be simultaneously displayed on the display section 14.

The central processing device 11 analyzes the name of the kind of the abnormal biological information waveform, such as the PAF (Paroxysmal Atrial Fibrillation), the duration time when the arrhythmia waveform is continued, the number of continuous beats of arrhythmia which is the number of heart beats included in the duration time, and the BPM (Beat Per Minute) in the duration time, based on the electrocardiogram. The central processing device 11 may cause the name of the kind of the abnormal biological information waveform, duration time of arrhythmia, number of continuous beats of arrhythmia, and BPM in the duration time, to be displayed simultaneously with the initial and last arrhythmia waveforms on the display section 14.

Figure 2:
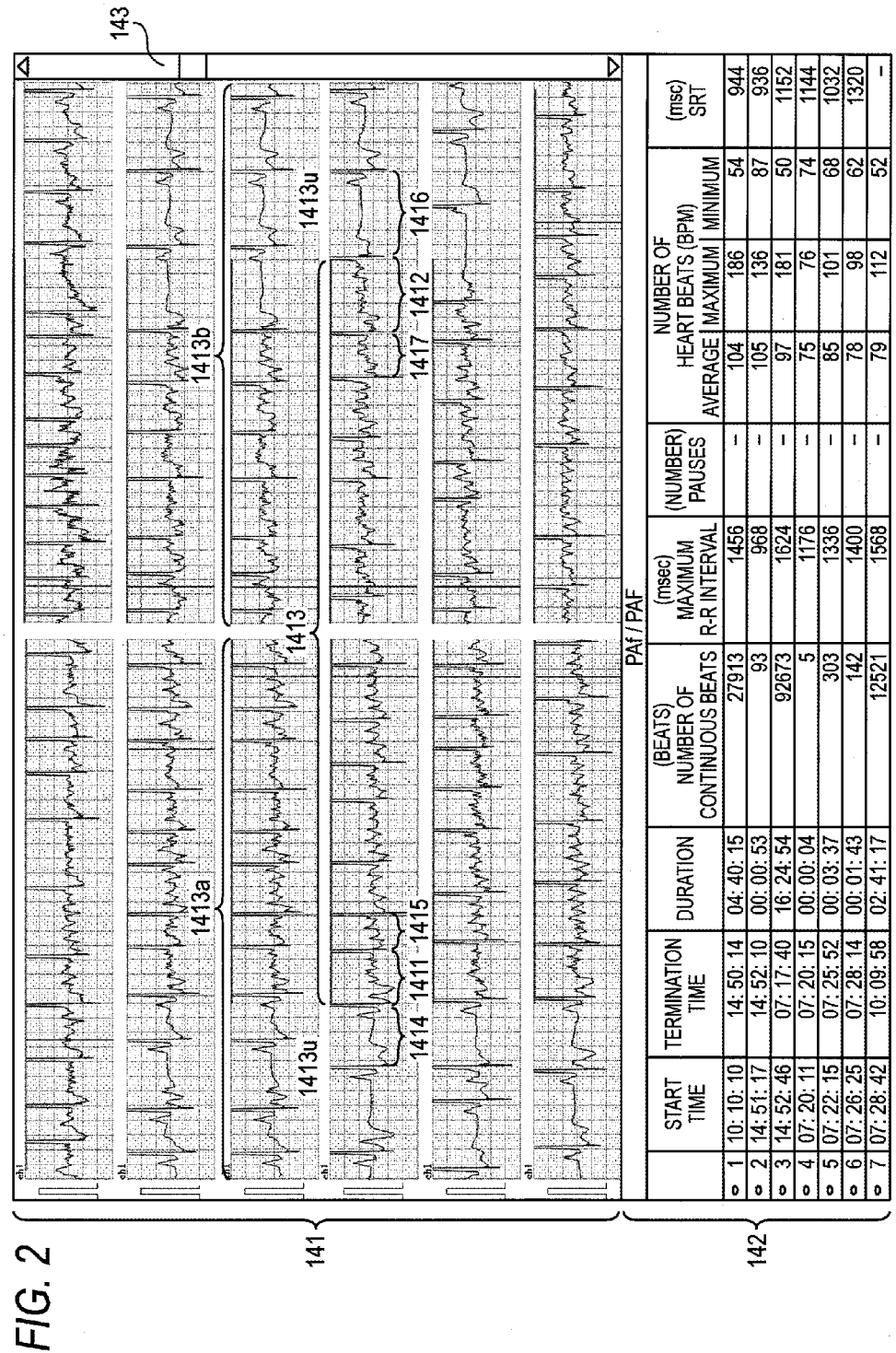
FIG. 2 is a view showing a display screen on which the initial and last arrhythmia waveforms included in abnormal waveform groups of an electrocardiogram are simultaneously displayed in a display section of the biological information displaying apparatus.

FIG. 2 is a view showing a display screen on which the initial and last arrhythmia waveforms included in abnormal waveform groups of the electrocardiogram are simultaneously displayed in the display section of the biological information displaying apparatus. Although FIG. 2 shows only electrocardiogram waveforms of one (ch 1) of a plurality of leads, the display can be switched to display an electrocardiogram produced by another lead of the biological information displaying apparatus 10.

As shown in FIG. 2, in a waveform display area 141 of the display section 14, the initial arrhythmia waveform 1411 and last arrhythmia waveform 1412 which are included in abnormal waveform groups 1413 of the electrocardiogram are displayed for each of the abnormal waveform groups 1413 which are intermittently produced, while being juxtaposed in, for example, the vertical direction of the display screen. Moreover, the initial arrhythmia waveform 1411 and the last arrhythmia waveform 1412 are displayed together with respective adjacent electrocardiogram waveforms 1414 to 1417 (namely, adjacent arrhythmia waveforms 1415, 1417 and adjacent normal electrocardiogram waveforms 1414, 1416). The initial arrhythmia waveform 1411 is included in a first waveform group 1413a, and the last arrhythmia waveform 1412 is included in a second waveform group 1413b.

Horizontal lines 1413u indicating an abnormal waveform group are displayed on the abnormal waveform groups 1413 displayed in the waveform display area 141.

When the user operates a scroll bar 143, for example, the initial and last arrhythmia waveforms can be simultaneously displayed with respect to all of the abnormal waveform groups 1413 which are intermittently produced.

Another scroll bar may be added below each of the electrocardiogram waveforms in FIG. 2, and the first waveform group 1413a and the second waveform group 1413b may be scrolled by operating the scroll bar so that waveforms before and after the waveform groups are displayed. According to the configuration, a change of the rhythm at the initial timing of the occurrence of arrhythmia, and that just before termination of arrhythmia can be checked for a longer time. Moreover, it is possible to check the certainty of arrhythmia which is detected and displayed by the biological information displaying apparatus 10.

As shown in FIG. 2, parameters of arrhythmia for each of arrhythmia periods which are durations of arrhythmia are displayed in the form of an arrhythmia period list in an arrhythmia period list display area 142 of the display section 14. Namely, the start time of arrhythmia when the initial arrhythmia waveform 1411 included in each of the abnormal waveform groups 1413 starts to be produced, the termination time of arrhythmia when the last arrhythmia waveform 1412 finishes to be produced, the duration of arrhythmia, the number of continuous beats of arrhythmia, the maximum RR interval, the number of heart beats in the duration, and the name of the kind of the abnormal biological information waveform are displayed. The SRT (Sinus Recovery Time) which is the period of time from termination of production of the last arrhythmia waveform to the timing when, after extinction of this last arrhythmia waveform, the next normal arrhythmia waveform is produced is further displayed in the arrhythmia period list display area 142.

Furthermore, a compressed waveform of all the period of the measured electrocardiogram may be displayed on the display section 14.

Conventionally, first, the initial arrhythmia waveform is displayed in a waveform display area by clicking the start time of arrhythmia in the arrhythmia period list displayed in an arrhythmia period list display area, and thereafter the last arrhythmia waveform is displayed in the waveform display area by clicking the termination time of arrhythmia. In the conventional art, namely, the initial and last arrhythmia waveforms in the duration are caused one by one by clicking to be individually displayed, and then the initial and last arrhythmia waveforms are checked independently from each other. In the conventional art, therefore, it is difficult to check rapidly and easily the initial and last arrhythmia waveforms, and it is impossible to check rapidly and easily a rhythm change at the initial timing of and before the occurrence of arrhythmia, and just before and after termination of arrhythmia.

In the case where arrhythmia occurs frequently and intermittently, conventionally, a clicking operation must be repeatedly performed in order to display the initial and last arrhythmia waveforms in each of durations of arrhythmia. In the conventional art, therefore, a relatively long time is required to check a rhythm change in an electrocardiogram before and after the occurrence of arrhythmia, and before and after the termination, with respect to all durations of arrhythmia.

Even in the case where arrhythmia occurs frequently and intermittently, conventionally, the arrhythmia waveform is individually displayed with respect to each of durations of arrhythmia. When the correctness of a detection result detected as an arrhythmia waveform is to be checked, therefore, the checking is performed while the waveform is individually displayed with respect to all durations of arrhythmia, irrespective of whether the detection result is required to be corrected or not. Therefore, a relatively long time is required to correct the detection result.

In the embodiment, by contrast, the first waveform group 1413a consisting of continuous biological information waveforms including: the initial arrhythmia waveform 1411 in a duration when arrhythmia waveforms are continued; and the biological information waveform 1414 produced just before the production of the initial abnormal biological information waveform, and the second waveform group 1413b consisting of continuous biological information waveforms including: the abnormal biological information waveform 1412 which is last produced; and the biological information waveform 1416 produced just after the production of the last abnormal biological information waveform are simultaneously displayed. With respect to each of the arrhythmia waveform groups 1413, therefore, rhythm changes before and after the occurrence of arrhythmia, and before and after the termination can be checked easily and instantaneously in a visual manner.

In the embodiment, the initial arrhythmia waveform 1411 and last arrhythmia waveform 1412 which are included in each of durations of arrhythmia are displayed while being juxtaposed in, for example, the vertical direction. Even in the case where arrhythmia occurs frequently and intermittently, therefore, the time required for checking a rhythm change before and after the occurrence of arrhythmia, and before and after the termination can be shortened with respect to all durations of arrhythmia.

In the configuration where the initial arrhythmia waveform 1411 and last arrhythmia waveform 1412 in a plurality of durations of arrhythmia are displayed in juxtaposition with each other, only an analysis result which is among results analyzed as an arrhythmia waveform by the central processing device 11, and which is necessary to be corrected can be selected to be easily corrected. As an example of correction of an analysis result by the central processing device 11, there is a case where, when the user determines that one arrhythmia period is an error one produced by the central processing device 11 due to noises imposed on an electrocardiogram waveform, the arrhythmia period is deleted from the arrhythmia period list.

The central processing device 11 may identify an arrhythmia waveform which is among detected arrhythmia waveforms, and which is necessary to be corrected, based on the measured continuous electrocardiogram waveforms, and cause the identified arrhythmia waveform to be displayed in an identifiable manner on the display section 14. For example, the central processing device 11 may analyze frequency components of detected arrhythmia waveforms, and identify an arrhythmia waveform having high-frequency components which exceed a threshold, as an arrhythmia waveform on which noises are superimposed, which is therefore low in reliability, and in which the detection result must be corrected. In the display section 14, an arrhythmia waveform that is identified by the central processing device 11 as an arrhythmia waveform in which the detection result must be corrected can be displayed in an identifiable manner by, for example, blinking.

In the case where the rhythm change between the initial and last arrhythmia waveforms exceeds a threshold, the central processing device 11 may cause the initial and last arrhythmia waveforms in which the rhythm change exceeds the threshold, to be displayed together with electrocardiogram waveforms adjacent thereto respectively on the display section 14 in an identifiable manner.

Returning to FIG. 1, the other components of the biological information displaying apparatus 10 will be described.

The internal storage device 12 may be configured by a RAM (Random Access Memory), a ROM (Read Only Memory), and an HDD (Hard Disk Drive).

The internal storage device 12 stores various programs for enabling the central processing device 11 to control the components of the internal storage device 12, and analyzing a measured electrocardiogram, and various data such as the data of the electrocardiograms which are read from the external storage device 20, and results of the electrocardiogram analysis performed by the central processing device 11.

The display control section 13 controls and drives the display section 14 based on the control by the central processing device 11, thereby causing the display section 14 to display images and the like.

The display section 14 may be configured by a liquid crystal display device.

The display section 14 is controlled and driven by the display control section 13 to simultaneously display the initial arrhythmia waveform 1411 and last arrhythmia waveform 1412 in arrhythmia periods which are detected by the electrocardiogram analysis performed by the central processing device 11. At the same time, the display section 14 displays the arrhythmia period list in which parameters of arrhythmia for each of arrhythmia periods are displayed. At the same time, the display section 14 can further display a compressed waveform of all the period of the electrocardiogram.

Figure 3:
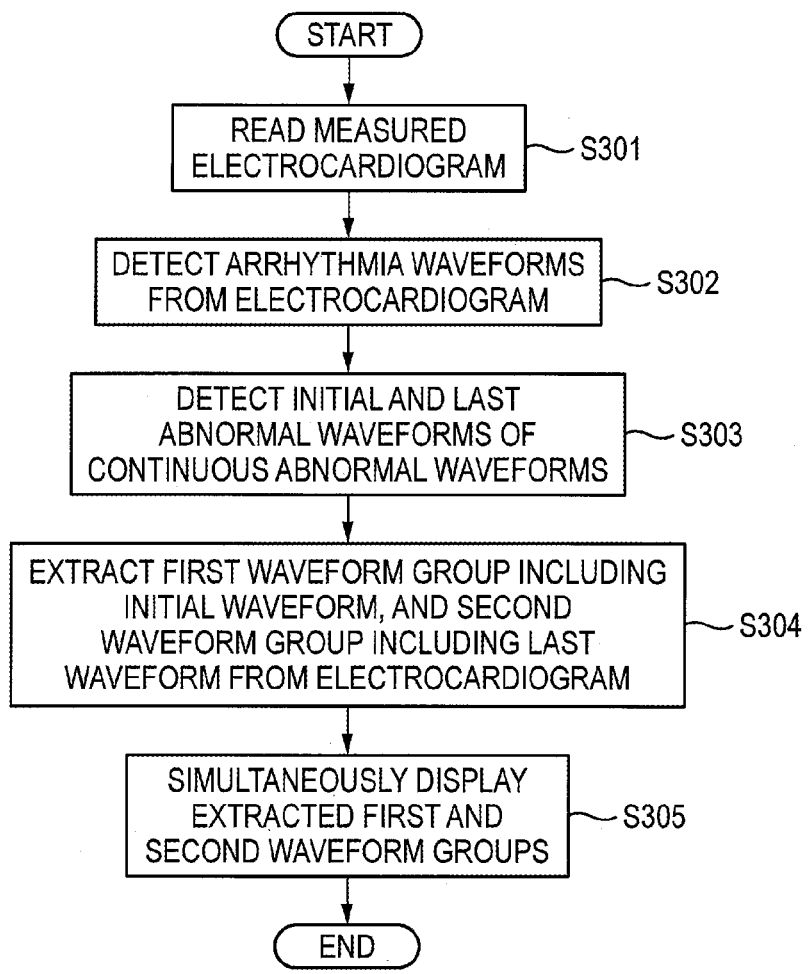
FIG. 3 is a view showing a flowchart of a biological information displaying method of the first embodiment of the presently disclosed subject matter.

FIG. 3 is a view showing a flowchart of a biological information displaying method of the embodiment. The flowchart is implementable based on programs in the biological information displaying apparatus 10 of the embodiment.

The central processing device 11 of the biological information displaying apparatus 10 reads a measured electrocardiogram from the external storage device 20 (S301).

The central processing device 11 analyzes the electrocardiogram which is read in step S301, and compares the basic waveform pattern of an arrhythmia waveform which is previously recorded in the internal storage device 12, with the measured electrocardiogram waveform, thereby detecting arrhythmia waveforms (S302).

The central processing device 11 detects the initial arrhythmia waveform 1411 and the last arrhythmia waveform 1412 from abnormal arrhythmia waveforms included in each duration in which the arrhythmia waveforms detected in step S302 are continuous (S303).

The central processing device 11 extracts the first waveform group 1413a including the initial arrhythmia waveform 1411 detected in step S303, and the electrocardiogram waveforms 1414, 1415 adjacent thereto, from the electrocardiogram. Furthermore, the central processing device 11 further extracts the second waveform group 1413b including the last arrhythmia waveform 1412 and the electrocardiogram waveforms 1416, 1417 adjacent thereto, from the electrocardiogram (S304).

The central processing device 11 causes the first waveform group 1413a and second waveform group 1413b which are extracted from the electrocardiogram in step S304, to be simultaneously displayed on the display section 14.

The embodiment achieves the following effects.

Abnormal biological information waveforms are detected from continuous biological information waveforms. The first waveform group consisting of continuous biological information waveforms including: an abnormal biological information waveform which is produced initially in abnormal biological information waveforms that are produced in a duration when the abnormal biological information waveforms are continued; and a biological information waveform which is produced just before the production of the initial abnormal biological information waveform, and a second waveform group consisting of continuous biological information waveforms including: an abnormal biological information waveform which is last produced; and a biological information waveform which is produced just after the production of the last abnormal biological information waveform are simultaneously displayed. According to the configuration, even in the case where arrhythmia continuously occurs for a long time, the waveforms at the initial timing of and before the occurrence of arrhythmia, and those just before and after termination of arrhythmia can be compared to each other at one time. Therefore, a change of the rhythm can be checked easily and instantaneously.

In the displaying unit, the first and second waveform groups can be simultaneously displayed while being laterally juxtaposed by setting the time axes to be parallel to each other. According to the configuration, the waveforms at the initial timing of the occurrence of arrhythmia, and just before termination of arrhythmia can be displayed corresponding to the occurrence times. Therefore, rhythm changes before and after the occurrence of arrhythmia, and before and after the termination can be checked easily and instantaneously while recognizing the time sequence relationship between the occurrence times of the waveforms.

Furthermore, the displaying unit simultaneously displays the first and second waveform groups with respect to two or more durations detected by the analyzing unit. Even in the case where arrhythmia occurs frequently and intermittently, therefore, the time required for checking a rhythm change before and after the occurrence of arrhythmia, and that before and after the termination can be shortened with respect to all durations. Moreover, the initial arrhythmia waveform and last arrhythmia waveform in a plurality of durations of arrhythmia are displayed in juxtaposition with each other, and therefore only an analysis result which is among results analyzed as a arrhythmia waveform, and which is necessary to be corrected can be selected to be easily corrected.

Based on the measured continuous biological information waveforms, the analyzing unit further analyzes at least one of the name of the kind of the abnormal biological information waveform, the duration time, the number of heart beats, and the number of continuous beats with respect to each of the detected waveform groups. Then, the waveform displaying unit displays these parameters for each of the durations together with the first and second waveform groups. Therefore, a rhythm change before and after the occurrence of arrhythmia, and that before and after the termination can be checked easily and quickly together with the parameters in each durations.

Furthermore, the analyzing unit identifies a biological information waveform which is among the detected abnormal biological information waveforms, and in which a detection result is necessary to be corrected, based on the measured continuous biological information waveforms, and causes the identified biological information waveform to be displayed in an identifiable manner on the displaying unit. Therefore, the user can easily check an abnormal biological information waveform in which there is a possibility of erroneous detection, and perform correction.

The analyzing unit further analyzes whether a rhythm change between an abnormal biological information waveform included in the first waveform group, and that included in the second waveform group exceeds a threshold or not, and causes the first and second waveform groups in which it is determined that the rhythm change exceeds the threshold, to be displayed on the display section in an identifiable manner. Therefore, the user can easily check an arrhythmia waveform in which a large rhythm change occurs between the waveforms at the initial timing of the occurrence of arrhythmia, and just before termination of arrhythmia.

Second Embodiment

A biological information displaying apparatus and method of a second embodiment of the presently disclosed subject matter will be described.

The present embodiment is different from the first embodiment in that, in the embodiment, the duration time, the number of heart beats, or a change of biological information occurring in the duration time is displayed as an image on the display section, in at least one of locations between the first and second waveform groups, in front of the first waveform group, and in rear of the second waveform group. The other configuration of the embodiment is identical with that of the first embodiment, and therefore duplicated description is omitted or simplified. For example, the change of biological information is a change of various parameters of an electrocardiogram waveform, such as the RR interval, that of various parameters of a respiratory waveform, or that of the blood oxygen saturation.

Figure 4A:
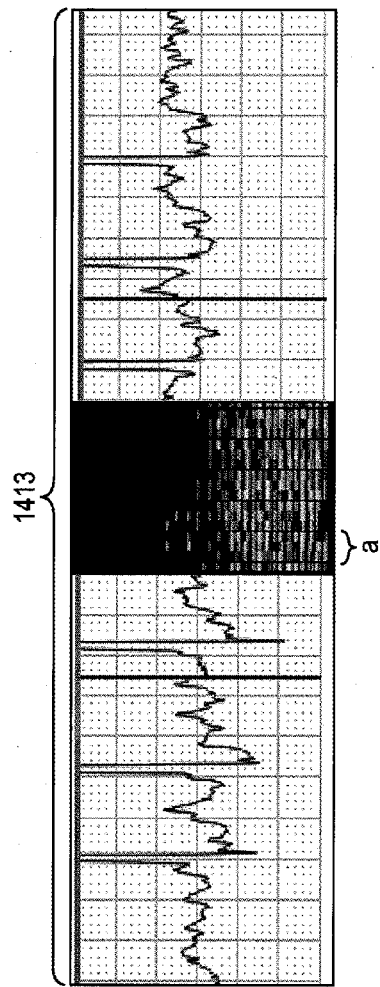
FIGS. 4A to 4C are views each showing a part of the state of the display section which displays images showing a change and the like of an electrocardiogram that are caused in a duration between the initial and last arrhythmia waveforms.
Figure 4B:
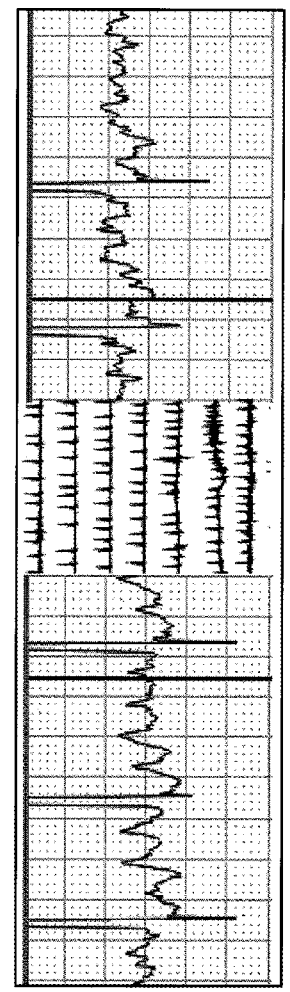
Figure 4C:
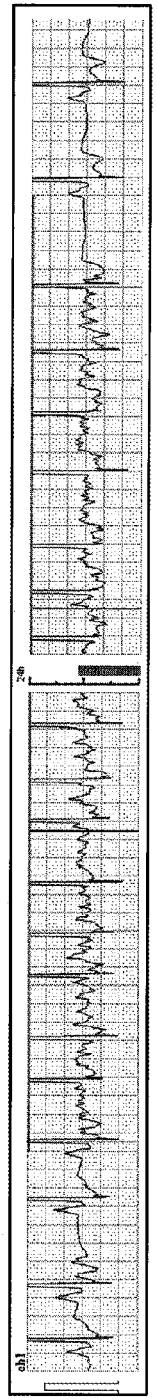

FIGS. 4A to 4C are views each showing a part of the state of the display section which displays images showing a change and the like of an electrocardiogram that are caused in a duration between the initial and last arrhythmia waveforms.

In FIG. 4A, in the middle of the abnormal waveform group 1413 consisting of arrhythmia waveforms in a duration of arrhythmia, a graph which is an image showing a change of the RR interval occurring in the duration is shown. The graph is shown between the initial arrhythmia waveform 1411 and last arrhythmia waveform 1412 which are not shown.

In the graph of FIG. 4A, the vertical axis represents time and the horizontal axis represents RR intervals of the electrocardiogram waveform. A plurality of region each having width "a" (time range) and height "b" (RR interval range) are arranged on the graph. The brightness of the region is determined in accordance with the number of arrhythmia waveforms existing in the time range "a" and the RR interval range "b". For example, the width "a" corresponds to 5 minutes. For example, the smaller the number of arrhythmia waveforms in the region is, the lower the brightness of the region becomes. In the case where low-brightness (dark) indications are dispersed in a wide range of the ordinate (FIG. 4A shows a graph in this case), therefore, it is possible to easily check in a visual manner that the dispersion of RR intervals is large. By contrast, in the case where high-brightness (bright) indications are concentrated in a narrow range of the ordinate, it is possible to easily check in a visual manner that the dispersion of RR intervals is small.

Alternatively, the display indicating the number of arrhythmia waveforms belonging to a predetermined RR-interval range may be performed by changing the color in accordance with the number, for example, altering the color from a cold color to a warm color in accordance with increase of the number.

In FIG. 4B, in the middle of the abnormal waveform group 1413 consisting of arrhythmia waveforms in a duration of arrhythmia, compressed waveforms of the electrocardiogram in the duration are shown.

In the compressed waveforms, as more moving in the right direction in the figure, and in the downward direction, the time further elapses. Since the compressed waveforms are displayed in this way, it is possible to easily check in a visual manner the duration of arrhythmia and the number of heart beats.

In FIG. 4C, in the middle of the abnormal waveform group 1413 consisting of arrhythmia waveforms in a duration of arrhythmia, the time which is in the duration, and during which no arrhythmia waveform is shown is displayed as an image.

As shown in FIG. 4C, the bar graph indicates that the time which is in the duration, and during which no arrhythmia waveform is shown is about 13 hours. Since the time which is in the duration, and during which no arrhythmia waveform is shown is graphically illustrated in this way, it is possible to easily check in a visual manner the duration of arrhythmia.

The embodiment achieves the following effects.

The duration of an abnormal biological information waveform, the number of heart beats, or a change of biological information which occurs in the duration is displayed as an image between the initial and last arrhythmia waveforms. When information functioning as an index of the severity of the patient's symptoms is displayed in accordance with the kind of arrhythmia, as an image in the middle of each of abnormal waveform groups, therefore, it is possible to check visually and easily the information. Furthermore, the information is displayed as an image before production of the abnormal biological information waveform and/or after returning from the abnormal biological information waveform to a normal biological information waveform. According to the configuration, when information functioning as an index of a condition change after arrhythmia, or the condition of the load on the patient is displayed as an image before and after the abnormal waveform group, the information can be checked visually and easily.

Although the biological information displaying apparatus and method of the embodiments of the presently disclosed subject matter have been described, the presently disclosed subject matter is not limited to the above-described embodiments.

In the arrhythmia period list, for example, parameters related to the respiration, the snoring, the blood oxygen saturation (SPO2), the effort respiration, the body posture, and the brain wave may be displayed. According to the configuration, also in diagnosis of the sleep apnea syndrome, multifaceted and effective diagnosis can be rapidly performed.

One of the initial and last arrhythmia waveforms may be displayed in place of the initial and last respiratory waveforms in a duration when abnormal respiratory waveforms are continued. According to the configuration, different sets of biological information are checked at the start and termination of a duration when abnormal biological information waveforms are continued, and therefore diagnosis which is more multifaceted, and which is further highly reliable can be rapidly performed. In diagnosis of the sleep apnea syndrome, when the respiratory waveform is displayed at the start of a duration when abnormal biological information waveforms are continued, and the waveform of the blood oxygen saturation is displayed at the termination, it is possible to easily check a series of reactions of a living body from the timing when respiration is weakened, to that when the blood oxygen saturation is lowered.

Although, in the embodiments described above, the biological information displaying method is performed by the programs in the biological information displaying apparatus, part or all of operations which are performed by the programs may be executed by hardware such as an LSI (Large Scale Integration).

What is claimed is:

1. A biological information displaying apparatus comprising:
   an analyzing unit comprising an interface, and internal storage device, and a central processing device executing a program stored on the internal storage device for causing said central processing device to analyze measured continuous biological information waveforms read from an external storage device connected to said interface to detect abnormal biological information waveforms; and
   a display unit connected to said central processing device, wherein said program includes:
      first program instructions causing said display to display a first waveform group, said first waveform group generated by the central processing device, executing said first program instructions, from the continuous biological information waveform, such that said first waveform group is produced by clipping an initial abnormal biological information waveform of continuous abnormal information waveforms and a biological information waveform immediately before the initial abnormal biological information waveform, and
      second program instructions causing said display to display, simultaneous with said first waveform group, a second waveform group generated by the central processing device, executing said second program instructions, from the continuous biological information waveforms, such that said second waveform group is produced by clipping a final abnormal biological information waveform of the continuous abnormal information waveforms and a biological information waveform immediately after the final abnormal biological information waveform.

2. The biological information displaying apparatus according to claim 1, wherein the display unit simultaneously displays the first waveform group and the second waveform group while being laterally juxtaposed by setting time axes to be parallel to each other.

3. The biological information displaying apparatus according to claim 1, wherein the display unit simultaneously displays the first waveform group and the second waveform group with respect to two or more durations of abnormal biological information waveforms detected by the analyzing unit.

4. The biological information displaying apparatus according to claim 1,
   wherein based on the measured continuous biological information waveforms, with respect to each of the durations, the analyzing unit further analyzes at least one of a name of a kind of the abnormal biological information waveform, the duration time, a number of heart beats, and a number of continuous beats, and the waveform displaying unit displays at least one of the name of the kind of the abnormal biological information waveform, duration time, number of heart beats, and number of continuous beats which are analyzed by the analyzing unit, for each of the durations together with the first waveform group and the second waveform group.

5. The biological information displaying apparatus according to claim 1, wherein the analyzing unit identifies a biological information waveform which is among the detected abnormal biological information waveforms, and in which a detection result is necessary to be corrected, based on the measured continuous biological information waveforms, and the displaying unit displays the abnormal biological information waveform that is identified by the analyzing unit as the biological information waveform in which correction is necessary, in an identifiable manner.

6. The biological information displaying apparatus according to claim 1, wherein the analyzing unit further analyzes whether a rhythm change between an abnormal biological information waveform included in the first waveform group, and an abnormal biological information waveform included in the second waveform group exceeds a threshold or not, and the display section displays the first waveform group and second waveform group in which the analyzing unit analyzes that the rhythm change exceeds the threshold, in an identifiable manner.

7. The biological information displaying apparatus according to claim 1, wherein the display section displays the duration time of the abnormal biological information waveform, the number of heart beats, or a change of biological information occurring in the duration time, as an image in at least one of locations between the first waveform group and the second waveform group, in front of the first waveform group, and in rear of the second waveform group.

8. The biological information displaying apparatus according to claim 1, wherein the analyzing unit analyzes a plurality of continuous biological information waveforms which are measured at a same time, and which are different from each other, to detect respective abnormal biological information waveforms, and the biological information waveforms constituting the first waveform group, and the biological information waveforms constituting the second waveform group are biological information waveforms which are different from each other, the first waveform group and the second waveform group being displayed by the display unit.

9. A biological information displaying method using a biological information displaying apparatus including a central processing device and an internal storage device storing a program, said method comprising the steps of:

(a) the central processing device including an interface and executing the program causing said central processing device to analyze measured continuous biological information waveforms retrieved from an external device connected to said interface to detect abnormal biological information waveforms; and (b) simultaneously displaying first and second waveforms on a display connected to said central processing device, wherein said program includes:

first program instructions causing said display to display the first waveform group, said first waveform group generated by the central processing device, executing said first program instructions, from the continuous biological information waveforms, such that said first waveform group is produced by clipping an initial abnormal biological information waveform of continuous abnormal information waveforms and a biological information waveform immediately before the initial abnormal biological information waveform, and second program instructions causing said program to display, simultaneous with said first waveform group, a second waveform group generated by the central processing device, executing said second program instructions, from the continuous biological information waveforms, such that said second waveform group is produced by clipping a final abnormal biological information waveform of the continuous abnormal information waveforms and a biological information waveform immediately after the final abnormal biological information waveform.

10. The biological information displaying method according to claim 9, wherein, in the step (b), the first waveform group and the second waveform group are displayed while being laterally juxtaposed by setting time axes to be parallel to each other.

11. The biological information displaying method according to claim 9, wherein, in the step (b), the first waveform group and the second waveform group are simultaneously displayed with respect to two or more durations of abnormal biological information waveforms detected in the step (a).

12. The biological information displaying method according to claim 9, wherein in the step (a), based on the measured continuous biological information waveforms, with respect to each of the durations, at least one of a name of a kind of the abnormal biological information waveform, the duration time, a number of heart beats, and a number of continuous beats is analyzed, and in the step (b), at least one of the name of the kind of the abnormal biological information waveform, duration time, number of heart beats, and number of continuous beats which are analyzed in the step (a) is displayed for each of the durations together with the first waveform group and the second waveform group.

13. The biological information displaying method according to claim 9, wherein in the step (a), a biological information waveform which is among the detected abnormal biological information waveforms, and in which a detection result is necessary to be corrected is identified based on the measured continuous biological information waveforms, and in the step (b), the abnormal biological information waveform that is identified in the step (a) as the biological information waveform in which correction is necessary, in an identifiable manner.

14. The biological information displaying method according to claim 9, wherein in the step (a), it is further analyzed whether a rhythm change between an abnormal biological information waveform included in the first waveform group, and an abnormal biological information waveform included in the second waveform group exceeds a threshold or not, and in the step (b), the first waveform group and second waveform group in which it is analyzed in the step (a) that the rhythm change exceeds the threshold are displayed in an identifiable manner.

15. The biological information displaying method according to claim 9, wherein, in the step (b), the duration time of the abnormal biological information waveform, the number of heart beats, or a change of biological information occurring in the duration time is displayed as an image in at least one of locations between the first waveform group and the second waveform group, in front of the first waveform group, and in rear of the second waveform group.

16. The biological information displaying method according to claim 9, wherein in the step (a), a plurality of continuous biological information waveforms which are measured at a same time, and which are different from each other are analyzed to detect respective abnormal biological information waveforms, and the biological information waveforms constituting the first waveform group, and the biological information waveforms constituting the second waveform group are biological information waveforms which are different from each other, the first waveform group and the second waveform group being displayed in the step (b).

* * * * *